(12) United States Patent
von Bohl

(10) Patent No.: US 11,713,456 B2
(45) Date of Patent: Aug. 1, 2023

(54) ISOLATION OF NUCLEIC ACIDS FROM ENVIRONMENTAL SAMPLES USING MAGNETIC PARTICLES

(71) Applicant: Axagarius GmbH & Co. KG, Dueren (DE)

(72) Inventor: Andreas von Bohl, Aachen (DE)

(73) Assignee: AXAGARIUS GMBH & CO. KG, Düren (DE)

( * ) Notice: Subject to any disclaimer, the term of this patent is extended or adjusted under 35 U.S.C. 154(b) by 112 days.

(21) Appl. No.: 17/225,263

(22) Filed: Apr. 8, 2021

(65) Prior Publication Data

US 2021/0317438 A1 Oct. 14, 2021

(30) Foreign Application Priority Data

Apr. 8, 2020 (DE) .................... 20 2020 109 837.5

(51) Int. Cl.
*C12N 15/10* (2006.01)
(52) U.S. Cl.
CPC ................ *C12N 15/1013* (2013.01)
(58) Field of Classification Search
None
See application file for complete search history.

(56) References Cited

U.S. PATENT DOCUMENTS

| 10,457,931 B2 | 10/2019 | Heymans et al. |
| 2017/0292122 A1 | 10/2017 | Heymans et al. |
| 2018/0195057 A1 | 7/2018 | Vlassov et al. |

FOREIGN PATENT DOCUMENTS

| DE | 10 2016 106 271 B1 | 10/2017 |
| DE | 10 2017 222 295 A1 | 6/2019 |
| EP | 1 502 951 A1 | 2/2005 |
| EP | 1 526 176 A1 | 4/2005 |
| EP | 1 626 085 A1 | 2/2006 |
| EP | 1 756 136 B1 | 10/2014 |
| WO | 2017 044827 A1 | 3/2017 |

OTHER PUBLICATIONS

Jin et al. Biosensors and Bioelectronics (2018), vol. 111, pp. 66-73.*

* cited by examiner

*Primary Examiner* — Patrick T Lewis
(74) *Attorney, Agent, or Firm* — Norris McLaughlin, P.A.

(57) ABSTRACT

The invention comprises methods for isolating nucleic acids, such as DNA and RNA, while enzyme-inhibiting polyanions are reduced at the same time, using a non-alcoholic binder solution that is not based on chaotropic salts, and a washing solution containing an amine compound, and kits suitable for such a method, comprising the mentioned binder solution and washing solution.

35 Claims, 2 Drawing Sheets

Specification includes a Sequence Listing.

SEQUENCE LISTING

<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<221> NAME/KEY: misc_feature
<223> OTHER INFORMATION: Primer

<400> SEQUENCE: 1
gggttaagtc ccgcaacga                                             19

<210> SEQ ID NO 2
<211> LENGTH: 22
<212> TYPE: DNA
<213> ORGANISM: Artificial Sequence
<220> FEATURE:
<221> NAME/KEY: misc_feature
<223> OTHER INFORMATION: Primer

<400> SEQUENCE: 2
cattgtagca cgtgtgtagc cc                                         22

<210> SEQ ID NO 3
<211> LENGTH: 20
<212> TYPE: DNA
<213> ORGANISM: Artificial Sequence
<220> FEATURE:
<221> NAME/KEY: misc_feature
<223> OTHER INFORMATION: primer

<400> SEQUENCE: 3
agagtttgat cctggctcag                                            20

```
<210> SEQ ID NO 4
<211> LENGTH: 20
<212> TYPE: DNA
<213> ORGANISM: Artificial Sequence
<220> FEATURE:
<221> NAME/KEY: misc_feature
<223> OTHER INFORMATION: Primer

<400> SEQUENCE: 4
aaggaggtga tccagccgca                                              20
```

ISOLATION OF NUCLEIC ACIDS FROM ENVIRONMENTAL SAMPLES USING MAGNETIC PARTICLES

CROSS-REFERENCES TO RELATED APPLICATIONS

This application claims priority of German Patent Application No. 10 2020 109 837.5, filed Apr. 8, 2020.

The invention describes a method for isolating nucleic acids, such as DNA and RNA, using a non-alcoholic binder solution that is not based on chaotropic salts, which results is less binding of contaminants/humic substances, and to the use of a washing solution containing an amine compound, which further results in a depletion of contaminants/humic substances, and to kits suitable for such methods, comprising the mentioned binder solution and washing solution.

BACKGROUND OF THE INVENTION

The present invention relates to a method and a test kit for isolating nucleic acids from biological samples or environmental samples with reduction of enzyme-inhibiting polyanions.

The isolation of nucleic acids from environmental samples, such as sediments, soil, rock, sludge, compost, rotting biological substances, peat, archaeological remains, water, terrestrial or subterranean water, atmospheric or industrial water, dust, stool specimens or biofilms, is difficult, mainly because of the wide variety of contaminants or enzymatic inhibitors, such as the polyanionic humic substances. Above all, humic substances purified together with nucleic acids represent a major problem, because they can heavily interfere with the subsequent analytics, such as enzyme-based methods.

Humic substances are formed in natural processes in soils by the decomposition of organic material by microorganisms. The fulvic acids, having a molecular weight of <0.1 kDa, and the humic acids, having a significantly higher molecular weight of >2-300 kDa, represent the largest proportion of humic substances in soils. Humic acids, which are mostly of a dark brown to gray color, are soluble mainly in a neutral or alkaline medium because of the large number of hydroxy and carboxy groups they contain, while the fulvic acids, which are of a slightly yellowish to slightly brownish color, are soluble in both acid and alkaline mediums.

The typical contamination of nucleic acid extracts from soil samples with humic substances can be recognized by a brownish to yellowish discoloration. This contamination is not removed easily or without further operations. Thus, the specification EP-B-1756136 describes the separation of humic substances by a multistep precipitation method using at least two precipitant solutions. This method is complicated, not because of the several precipitations, but it also bears the risk that nucleic acids are in part also precipitated. The specification EP-A-3347491 also describes a method for separating off humic substances using a comparable precipitation, but in contrast to EP-B-1756136, it is not effected in two successive steps. Because of the properties of the precipitant agents, a precipitation of nucleic acids may occur here, too.

Both methods have in common that binder solutions containing chaotropic salts and alcohols are also employed, in addition to the precipitation of humic substances. The binding of nucleic acids, for example, to magnetic particles, is usually effected by the addition of a chaotropic salt and/or organic solvents, such as ethanol or isopropanol. Thus, EP-A-1502951, EP-A-1526176 and EP-A-1626085 (Agilent) describe methanol, ethanol, isopropanol and polyethylene glycol as organic binding enhancers in combination with a solution of a chaotropic salt for binding nucleic acids to a solid matrix.

DE-A-102017222295 discloses a chromatographic procedure for the removal of humic substances that avoids the use of such organic binding enhancers in the solutions for binding the nucleic acids to a solid matrix. The chromatographic procedure, however, employs chaotropic salts for the binding of the nucleic acids to a solid matrix and in the subsequent washing steps.

In the context of isolating nucleic acids from soil samples, the use of this kind of binder solution results in an entrainment of humic substances and thus in nucleic acid extracts with a brownish discoloration. Alternative methods that lead to a reduction of humic substances within the DNA extracts often include several steps, such as different precipitant solutions, or a mechanical prefiltration of the lysates.

Because of the known drawbacks of the existing solutions and the drawbacks of reagent systems based on chaotropic salts/alcohol, the focus was on alternative reagent systems that are substantially free of chaotropic salts and that generally result in a lower binding of humic substances by means of binder solutions and in an improved depletion of humic substances by means of washing solutions.

SUMMARY OF THE INVENTION

It has now been found that the use of a binder solution consisting of at least one cyclic alkylene carbonate or an alkylene glycol diacetate and a non-ionic surfactant has advantageous effects on the binding of DNA in the presence of humic substances to carboxylated magnetic particles. Further, it has now been found that the use of a washing solution containing an amine compound as described in the specification DE-B-102016106271 has advantageous effects on the depletion of humic substances against expectations. DE-B-102016106271 describes this washing solution for reducing endotoxins, so that it is not obvious to those skilled in the art that this washing solution should also be suitable for depleting humic substances.

The specific reagent systems for reducing humic substances that have been found are suitable, in combination with different lysis methods (mechanical lysis and enzymatic lysis), for the isolation of nucleic acids from a rather broad range of samples, such as environmental samples. Thus, the invention relates to:

(1) a method for isolating nucleic acids from a biological sample or environmental sample and depleting contaminants/humic substances from the biological sample, comprising (a) mechanically lysing said biological sample or environmental sample using a lysis buffer (hereinafter also referred to as "lysing solution");

(b1) precipitating a major part of the contaminants by adding a precipitant solution;

(b2) adding a binder solution comprising at least one organic solvent selected from cyclic $C_{2-4}$-alkylene carbonates, $C_{2-3}$-alkylene glycol diacetates, and derivatives thereof, and at least one non-ionic surfactant, and a nucleic acid-binding solid phase to the lysed sample, and separating the solid phase with the nucleic acids bound thereto;

(c) washing the separated solid phase with the nucleic acids bound thereto once or several times with the same or different washing solutions, wherein at least one washing solution contains an amine compound; and (d) desorbing the nucleic acids from the solid phase by adding an aqueous elution buffer;

(2) a preferred embodiment of aspect (1), wherein said binder solution is a binder solution that is free of chaotropic salts;

(3) the use of a binder solution for isolating nucleic acids from a biological sample or environmental sample, especially for a method according to aspect (1) or (2), comprising at least one cyclic $C_{2-4}$-alkylene carbonate, and/or one $C_{2-3}$-alkylene glycol diacetate, and at least one non-ionic surfactant; and (4) the use of one or more washing solutions for depleting humic substances, especially for a method according to aspect (1) or (2), comprising at least one amine compound and alcohol;

(5) a kit for isolating nucleic acids from a biological sample, especially for a method according to aspect (1) or (2), comprising a binder solution according to aspect (3) and a washing solution according to aspect (4), and optionally a solid phase that binds nucleic acids.

DETAILED DESCRIPTION OF THE INVENTION

Figure 1:
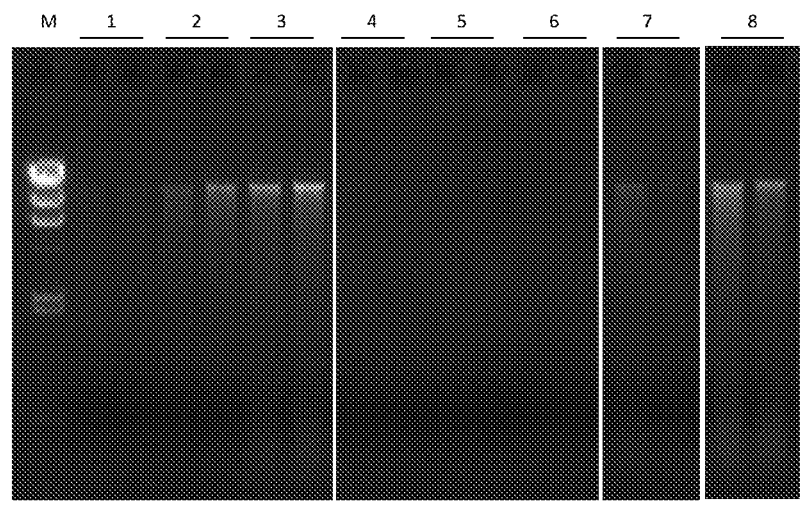
FIGS. 1, 2, 3 and 4 show results of Examples 1, 2, 3 and 4, respectively.

Aspects (1) and (2) of the invention relate to a method for isolating nucleic acids from a biological sample. This includes the isolation of DNA and RNA, and mixtures and derivatives thereof. The sample (e.g., soils) is lysed by mechanical lysis using a lysing solution. Such lysing solutions preferably contain, inter alia, a low concentration of sodium acetate 200 mM), sodium chloride 500 mM), and/or another anionic surfactant 2% (w/v) SDS (sodium dodecylsulfate)). Subsequently, by adding magnetic particles and the binding solution, the DNA is bound to the solid phase, in this case the magnetic particles. The solid phase is washed by contacting it with one or more washing solutions, and subsequently eluted from the solid phase.

In the method of aspect (1) of the invention, the lysis may be effected by mechanical lysis and by using a lysis solution, wherein said lysis solution preferably contains low concentrations of EDTA and/or an anionic surfactant.

"Solutions" within the meaning of the present invention need not necessarily contain inorganic or organic salts, they may be completely free thereof, like in the case of the binding buffer or some washing buffers, in which case they should be referred to correctly as compositions or mixtures. Thus, unless stated otherwise, the "solutions" within the meaning of the present invention consist of aqueous solutions or aqueous/alcoholic solutions (with ethanol or isopropanol as alcohol components, and an alcohol proportion of about 35 to about 100% (v/v)), admixed with sufficient amounts of suitable substances (e.g. inorganic or organic salts, or buffer substances known to those skilled in the art).

Preferably, in the binder solution, said cyclic $C_{2-4}$-alkylene carbonate is selected from butylene carbonate, propylene carbonate, ethylene carbonate, and derivatives thereof, and said $C_{2-3}$-alkylene glycol diacetate is selected from ethylene glycol diacetate, propylene glycol diacetate, and derivatives thereof. "Derivatives" within the meaning of the present invention include those of the mentioned compounds in which one or more of the hydrogen atoms of the carbon chain are independently replaced by $C_{1-3}$-alkyl, $C_{1-3}$-alkoxy, hydroxy or halogen substituents. Preferably, the binder solution contains at least one compound selected from butylene carbonate (BC) (CAS 4437-85-8), propylene carbonate (PC) (CAS 108-32-7), ethylene carbonate (EC) (CAS 96-49-1), ethylene glycol diacetate (EGDA) (CAS 111-55-7), and propylene glycol diacetate (PGDA) (CAS 623-84-7), wherein BC, PC, EC, and EGDA are particularly preferred.

Said at least one non-ionic surfactant is preferably selected from polyoxyethylene derivatives of sorbitan monolaureate, sorbitan monopalmitate, and sorbitan monooleate, and polyoxyethylene derivatives, i.e., compounds of the Tween® series, and polyoxyethylene derivatives of fatty alcohols, i.e., compounds of the Brij® series, wherein polyoxyethylene(20) sorbitan monolaureate (Tween®-20; CAS 9005-64-5) is particularly preferred.

Preferably, the ratio (v/v) of organic solvent (i.e., cyclic $C_{2-4}$-alkylene carbonate/$C_{2-3}$-alkylene glycol diacetate) to non-ionic surfactant, especially if the non-ionic surfactant is Tween®-20, is from about 80:20 to about 50:50, preferably from about 75:25 to about 55:45, and more preferably about 70:30. Preferably, in step (b), the nucleic acid-binding solid phase is magnetic carboxylated particles (carboxylated particles containing superparamagnetic particles in a range of sizes of from about 0.5 to about 10 μm).

In step (b), the amount of added binder solution as a ratio to the volume of lysed sample is from about 10:1 to 1:10, preferably from about 3:1 to 1:3, and more preferably from about 2:1 to 1:1 (v/v) (binder solution/solution:lysed sample). The amount of added solid phase as a ratio to the volume of lysed sample is from about 1:10 to about 1:50, preferably from about 1:20 to about 1:40, and more preferably about 1:25 (v/v) (solid phase:lysed sample).

According to aspect (2) of the invention, a binder solution that is free of chaotropic salts is used. Within the meaning of the present invention, "free of chaotropic salts" and "not containing chaotropic salts" means that no or negligible/ineffective amounts of chaotropic salts known to those skilled in the art according to the Hofmeister series, such as barium, calcium, sodium and guanidinium perchlorates, thiocyanates, isothiocyanates, iodides and perchloroacetates, and guanidine hydrochloride, are present in the respective solutions. Such solutions "free of chaotropic salts" may contain other salts that are not chaotropic, such as alkali, alkaline earth and ammonium salts or organic acids, of sulfates, or of chlorides. On the other hand, "containing chaotropic salts" within the meaning of the present invention means that not negligible/effective amounts of just such chaotropic salts are contained in the corresponding solution.

According to the present invention, not only the binder solution of step (b), but also the lysing solution of step (a), the washing solution(s) of step (c), and/or the elution buffer of step (d) may be free of chaotropic salts, wherein preferably neither the lysing solution of step (a), nor the binder solution of step (b), nor the elution buffer of step (d) contains chaotropic salts, and only one of the washing solutions of step (c) contains chaotropic salts.

Said washing solutions containing at least one amine compound (hereinafter also referred to as "washing solution (A)") in step (c) contains at least one organic amine compound having at least two carbon atoms and a molecular weight of ≤500 g/mol, and at least one solvent other than the amine compound, and/or has a pH (20° C.) within a range of from about pH 3.0 to about pH 8.5. The volume of the respective washing solution (A) is about 10 times to about 50 times that of the solid phase employed in step (b).

Said at least one organic amine compound is selected from a compound of the general formula (I)

$$N(R^1)(R^2)(R^3) \qquad (I),$$

wherein $R^1$, $R^2$ and $R^3$ are independently a hydrogen atom, a $(C_{1-6})$-alkyl group, a $(C_{1-6})$-monohydroxyalkyl group, a $(C_{2-6})$-dihydroxyalkyl group, or a $(C_{3-6})$-trihydroxyalkyl group, with the proviso that at least one of radicals $R^1$, $R^2$ and $R^3$ is not a hydrogen atom. The $(C_{1-6})$-alkyl group includes, but is not limited to, linear branched and circular $(C_{1-6})$-alkyl groups such as methyl, ethyl, propyl, iso-propyl, cyclopropyl, butyl, sec-butyl, tert-butyl, cyclobutyl, pentyl, sec-pentyl, neo-pentyl, cyclopentyl, hexyl, sec-hexyl and cyclohexyl groups. The $(C_{1-6})$-monohydroxyalkyl group includes, but is not limited to, the above-exemplified $(C_{1-6})$-alkyl groups additionally carrying a hydroxy group. The $(C_{2-6})$-dihydroxyalkyl group includes, but is not limited to, dihydroxyethyl, dihydroxypropyl, dihydroxypropyl and dihydroxybutyl groups. The $(C_{3-6})$-trihydroxyalkyl group includes, but is not limited to, tris-(hydroxymethyl)methyl and 2,2,2-tris(hydroxymethyl)ethyl groups. Preferably, said amine compound is selected from triethylamine, triethanolamine, 2-amino-2-(hydroxymethyl)propane-1,3-diol (TRIS), 2,2-bis(hydroxymethyl)-2,2',2"-nitrilotriethanol (BIS-TRIS), 1,3-bis[tris-(hydroxymethyl)methylamino]propane (BIS-TRIS propane), or combinations thereof, and more preferably is bis-tris and/or triethanolamine. Said solvent other than the amine compound may be a salt-containing water-alcohol mixture, or a salt-containing aqueous or alcoholic solution, or a salt-containing alcohol-water mixture, preferably an ethanol-water mixture (free of chaotropic salts). The washing solution(s) (A) of step c) may contain the organic amine compound in a concentration of from about 200 mmol/l to about 1000 mmol/l, preferably in a concentration of from about 200 mmol/l to about 800 mmol/l.

The additional washing solutions free of amine compounds (hereinafter also referred to as "washing solutions (B)") in step (c) include aqueous solutions containing (chaotropic) salts (including aqueous solutions containing chaotropic salts such as sodium perchlorate or guanidine hydrochloride), preferably aqueous solutions containing ethanol, or ethanol-water mixtures (e.g., 70% ethanol, 30% water, with or without the above mentioned chaotropic salts).

The volume of the respective washing solution (B) is preferably 10 times to 50 times that of the solid phase employed in step (b) (carboxylated particles containing superparamagnetic particles in a range of sizes of from about 0.5 to about 10 μm).

The elution solution of step (d) is preferably an alkaline low-salt buffer (for example, about 5 mM Tris/HCl, about pH 8.5). The volume of the elution buffer is preferably about once to about 20 times that of the solid phase employed in step (b).

In the following, a detailed procedure of the method according to the invention is outlined:

1. Lysis of a biological sample by mechanical lysis and the use of a lysing solution containing no chaotropic salts (consisting of about 0.4 to about 2.5% SDS (w/v), from about 10 to about 400 mM sodium acetate, and from about 10 to about 400 mM sodium chloride).

2. Addition of a precipitating agent for precipitating the major part of the contaminants (consisting of from about 1 to about 4 M potassium acetate).

3. Addition of a binder solution consisting of a cyclic alkylene carbonate or alkylene glycol diacetate, and a polysorbate in a ratio of about 70:30 (w/v), and magnetic carboxylated particles (carboxylated particles containing superparamagnetic particles in a range of sizes of from about 0.5 to about 10 μm) (for example, NucleoMag® B beads of the kit NucleoMag® Tissue (MACHEREY-NAGEL, REF: 744300.1), 24 μl) as a solid phase for binding the nucleic acid.

4. Depletion of humic substances and contaminants by one or more (chaotropic) salt-containing, ethanol-containing washing solutions (e.g., solutions W1, W2, W3, having a high content of chaotropic salt (e.g., sodium perchlorate or guanidine hydrochloride) of about 5 to about 10% (w/v), and an ethanol content of from about 30 to about 60%), and with at least one washing solution containing at least one amine compound having at least two carbon atoms and a molecular weight of ≤500 g/mol, and at least one (organic) solvent other than the amine compound.

5. The magnetic particles are washed using an alcoholic washing solution (e.g., 80% ethanol, 20% water (v/v)).

6. The nucleic acid is released from the magnetic particles using water or a slightly alkaline low-salt buffer (e.g., 5 mM Tris/HCl, pH 8.5).

The use of the above described binder solution in combination with the washing solution described is advantageous over other solution or reagent compositions, since they:

are less toxic or harmful and are thus more environmentally friendly;
reduce the use of chaotropic salts; and
allow for the same or better yields and purities of isolated DNA, depending on the sample material;
result in a reduction of humic substances in the eluate.

In addition to the binder solution and the nucleic acid-binding solid phase, the kit of aspect (4) may further contain one or more of the lysis solutions, the washing solutions that are free of amine compounds, and the elution buffer as defined above.

The term "about" as referred to herein refers to deviations from the basic value of 10%, or 5%, 3% or 1%, and of course exemplifies the exact value. The references mentioned herein are incorporated by reference in their entirety for all purposes.

The invention is further explained by means of the following Examples. However, these Examples do not by any means limit the claimed subject matter.

EXAMPLES

Materials and Methods

The following compounds and compositions were used in the following Examples: sodium dodecylsulfate (SDS) (>98.5%, Sigma-Aldrich), potassium acetate (≥99%, Sigma-Aldrich), sodium chloride (≥99.5%, Sigma-Aldrich), butylene carbonate (CAS 4437-85-8) (≥98.0%, TCI Chemicals), propylene carbonate (CAS 108-32-7) (99.7%, Sigma-Aldrich), ethylene carbonate (CAS 96-49-1) (>99.0%, TCI Chemicals), ethylene glycol diacetate (CAS 111-55-7) (≥99%, Sigma-Aldrich), propylene glycol diacetate (CAS 623-84-7) 99.7%, Sigma-Aldrich), Tween® 20 (Sigma-Aldrich), 40 (Sigma-Aldrich), and 80 (Sigma Aldrich), Brij® 58 (Sigma-Aldrich), Triton X-100 (Sigma-Aldrich), Span® 40 (Sigma-Aldrich), solution A (consisting of 100% isopropanol (v/v)), solution B (consisting of 65% ethylene glycol diacetate (v/v), and 35% Tween® 20 (v/v)), and solution C (consisting of 2.4 M sodium perchlorate and 60% ethanol (v/v)); solutions W1 and W2, consisting of 1.3 M sodium perchlorate and 35% ethanol (v/v), having a high content of chaotropic salt (5-20% (w/v)) and ethanol (20-35% (v/v)), solution W3 consisting of 3.2 M guanidine hydrochloride and 50% ethanol (v/v), solution W4 consisting of 50% isopropanol (v/v) and 8% triethanolamine (v/v) (pH 6), solution W5 consisting of 50% isopropanol (v/v) and 4% triethanolamine (v/v) (pH 6), solution W6 consisting of 50% isopropanol (v/v) and 400 mM bis-tris (pH 6), solution W7 consisting of 50% isopropanol (v/v) and 200 mM bis-tris (pH 6.5), and solution W8 consisting of 50% isopropanol (v/v) and 400 mM bis-tris (pH 6.5).

IMPLEMENTATION EXAMPLES

The exemplary experiments were performed according to the following protocol, unless stated otherwise. These describe a purification method according to the invention for a soil sample by way of example, and show the advantageous purification over standard methods.

Test Performance

Per charge, 250 mg of a soil sample was added to a reaction vessel with 1.5 g of ceramic beads. After adding a total of 1150 µl of a lysis buffer mixture, the cells contained in the sample were lysed by "bead beating" (fast agitation of the reaction vessels). The nucleic acid-containing supernatant, hereinafter referred to as "lysate", was separated from the ceramic beads and soil particles by a subsequent centrifugation, e.g., for about 10 min at about 8,000×g, and transferred into a new reaction vessel. The lysate was subsequently mixed with about 150 µl of a precipitation solution and incubated at about 4° C. or on ice for about 10 min for the precipitation of contaminants. After another centrifugation step, about 360 to about 500 µl of the respective binder solution and about 25 µl of a magnetic bead suspension (carboxylated particles containing superparamagnetic particles in a range of sizes of from about 0.5 to about 10 µm) (for example, NucleoMag® B beads of the kit NucleoMag® Tissue (MACHEREY-NAGEL, REF: 744300.1) were added to the cleared lysate in a new reaction vessel, and the mixture of lysate, beads and binder solution was thoroughly mixed by repeatedly pipetting it up and down. Optionally, other techniques, such as using a laboratory shaker or an automated magnetic particle processing device, can be used for the thorough mixing. After the mixing is complete, the magnetic particles are separated off using a static or automated magnetic separator, so that either the supernatant containing the lysate/binder solution can be separated off by aspiration, or the magnetic particles can be separated off by using a moveable magnetic separator. Subsequently, the magnetic particles are resuspended or thoroughly mixed in 600 µl of the respective washing solution, for example, by repeatedly pipetting up and down, shaking or other techniques. After the mixing is complete, a new separation of the magnetic particles from the respective washing buffer is effected by one of the techniques described above. In the further processing, three further washing steps were performed with the respective washing solutions (about 600 µl each) according to the principle described above, wherein an 80% ethanol-water mixture is used as the washing solution in the fourth washing step. After a drying step at room temperature for about 5 to about 10 min, the DNA was released from the magnetic particles by adding about 100 µl of an elution buffer (about 5 mM Tris/HCl, about pH 8.5), and separated off by means of a magnetic separator as described above.

Example 1

For each extraction, 200 mg of a soil sample was lysed as described in the Test performance. Subsequently, about 400 µl of the respective binder solution (see Table 1) and about 25 µl of NucleoMag® B beads (carboxylated particles containing superparamagnetic particles in a range of sizes of from about 0.5 to about 10 µm) per sample were added. Subsequently, the magnetic particles were incubated with the washing solutions W1, W2, W3 and 80% ethanol as described in the Test performance. After a drying step, the DNA was released from the magnetic particles by adding about 100 µl elution buffer (about 5 mM Tris/HCl, about pH 8.5), and separated off.

TABLE 1

| Variant | Binder solution Substance A | Binder solution Substance B | Photometric DNA yield [µg] (mean value) | Ct values (mean value) | Absorption at 300 nm (mean value) |
|---|---|---|---|---|---|
| 1 | BC 70% | Tween ® 20 30% | 0.2 | 18.46 | 0.02 |
| 2 | PC 70% | Tween ® 20 30% | 0.45 | 16.25 | 0.03 |
| 3 | EGDA 70% | Tween ® 20 30% | 1.00 | 15.27 | 0.03 |
| 4 | BC 100% | — | 0.20 | 20.63 | 0.02 |
| 5 | PC 100% | — | 0.20 | 21.47 | 0.02 |
| 6 | EGDA 100% | — | 0.20 | 19.93 | 0.02 |
| 7 | Tween 20 | — | 0.35 | 17.54 | 0.03 |
| 8 | Solution C | — | 1.60 | no amplification | 0.11 |

From the available data in Table 1, it can be seen that the use of a binder solution that is free of chaotropic salts and ethanol has advantageous effects on the isolation of nucleic acids from soil samples or samples rich in humic substances. A photometric measurement at 300 nm, which can be used as an indicator of a brown color, shows a very low absorption as compared to a binder solution containing chaotropic salts and alcohol. Further, the entrainment of humic substances was analyzed from the enzymatic inhibition within a qPCR. Those skilled in the art are aware that humic substances can inhibit enzymes such as thermostable DNA polymerases. In the present Example, a fragment of a 16s rRNA gene was amplified with the forward primer GGGTTAAGTCCCGCAACGA (SEQ ID NO: 1) and reverse primer CATTGTAGCACGTGTGTAGCCC (SEQ ID NO: 2), which are generic primers for Gram-positive and Gram-negative bacterial species (P. M. Kärkkäinen et al., Environ Monit; 12: 759-68 (2010)), by quantitative PCR using the SensiFAST™ SYBR® Lo-ROX kit of the company Bioline in a reaction volume of about 10 µl.

Here too, it can be seen that mixtures of BC, PC or EGDA and Tween® 20 have an advantage over binder solutions containing chaotropic salts and alcohol, since, despite approximately equal DNA quantities of variants 2-3 and 8 (see FIG. 1), an amplification could be detected only when said binder solution was used.

Example 2

For each extraction, about 200 mg of a soil sample was lysed as described in the Test performance. Subsequently, about 400 µl of the respective binder solution (see Table 1)

and about 25 μl of NucleoMag® B beads (carboxylated particles containing superparamagnetic particles in a range of sizes of from about 0.5 to about 10 μm) per sample were added. Subsequently, the magnetic particles were incubated with the washing solutions W1, W2, W3 and 80% ethanol as described in the Test performance. After a drying step, the DNA was released from the magnetic particles by adding about 100 μl elution buffer (about 5 mM Tris/HCl, about pH 8.5), and separated off.

TABLE 2

| Variant | Binder solution Substance A | Binder solution Substance B | Photometric DNA yield [μg] (mean value) | Ct values (mean value) | Absorption at 300 nm (mean value) |
|---|---|---|---|---|---|
| 1 | EGDA 70% | Tween® 20 30% | 1.15 | 13.44 | 0.051 |
| 2 | EGDA 70% | Tween® 40 30% | 1.15 | 13.59 | 0.062 |
| 3 | EGDA 70% | Tween® 80 30% | 1.05 | 13.41 | 0.059 |
| 4 | Solution C | | 2.00 | 22.59/no amplification | 0.104 |

From the available data in Table 2, it can be seen that the use of a binder solution that is free of chaotropic salts and alcohol has advantageous effects on the isolation of nucleic acids from soil samples or samples rich in humic substances. A photometric measurement at 300 nm, which can be used as an indicator of a brown color, shows a very low absorption as compared to a binder solution containing chaotropic salts and ethanol. Further, the entrainment of humic substances was analyzed from the enzymatic inhibition within a qPCR. Those skilled in the art are aware that humic substances can inhibit enzymes such as thermostable DNA polymerases. In the present Example, a fragment of a 16s rRNA gene was amplified with the forward primer GGGTTAAGTCCCGCAACGA (SEQ ID NO: 1) and reverse primer CATTGTAGCACGTGTGTAGCCC (SEQ ID NO: 2) by quantitative PCR using the SensiFAST™ SYBR® Lo-ROX kit of the company Bioline in a reaction volume of about 10 μl.

Figure 2:
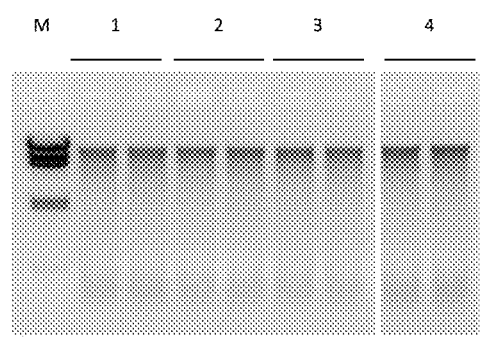

Here too, it can be seen that mixtures of EGDA and polysorbates have an advantage over binder solutions containing alcohol, since, despite a comparable DNA quantity (see FIG. 2), an amplification by means of qPCR could be achieved only when said binder solution was used.

Example 3

For each extraction, about 200 mg of a soil sample was lysed as described in the Test performance. Subsequently, about 400 μl of binder solution B and about 25 μl of NucleoMag® B beads (carboxylated particles containing superparamagnetic particles in a range of sizes of from about 0.5 to about 10 μm) per sample were added. Subsequently, the magnetic particles were incubated with the respective washing solutions (see Table 3) as described in the Test performance. After a drying step, the DNA was released from the magnetic particles by adding about 100 μl elution buffer (about 5 mM Tris/HCl, about pH 8.5), and separated off.

TABLE 3

| | Washing solution 1/2 | Washing solution 3 | Washing solution 4 | Photometric DNA yield [μg] (mean value) | Ct values (mean value) | Absorption at 300 nm (mean value) |
|---|---|---|---|---|---|---|
| Var. 1 | W5 (600 μl) | W3 (600 μl) | 80% EtOH (v/v) (600 μl) | 1.50 | 14.94 | 0.137 |
| Var. 2 | W4 (600 μl) | W3 (600 μl) | 80% EtOH (v/v) (600 μl) | 1.45 | 14.73 | 0.136 |
| Var. 3 | W6 (600 μl) | W3 (600 μl) | 80% EtOH (v/v) (600 μl) | 1.35 | 14.35 | 0.111 |
| Var. 4 | W7 (600 μl) | W3 (600 μl) | 80% EtOH (v/v) (600 μl) | 1.25 | 14.52 | 0.120 |
| Var. 5 | W8 (600 μl) | W3 (600 μl) | 80% EtOH (v/v) (600 μl) | 1.45 | 14.55 | 0.118 |
| Var. 6 | W1/W2 (600 μl) | W3 (600 μl) | 80% EtOH (v/v) (600 μl) | 1.05 | no amplification | 0.147 |

From the available data in Table 3, it can be seen that the use of an amine-containing washing solution has advantageous effects on the isolation of nucleic acids from soil samples or samples rich in humic substances but does not yet yield an optimum result. A photometric measurement at 300 nm, which can be used as an indicator of a brown color, shows a slightly lower absorption as compared to washing solutions containing chaotropic salts and ethanol. Further, the entrainment of humic substances was analyzed from the enzymatic inhibition within a qPCR. Those skilled in the art are aware that humic substances can inhibit enzymes such as thermostable DNA polymerases. In the present Example, a fragment of a 16s rRNA gene was amplified with the forward primer GGGTTAAGTCCCGCAACGA (SEQ ID NO: 1) and reverse primer CATTGTAGCACGTGTGTAGCCC (SEQ ID NO: 2) by quantitative PCR using the SensiFAST™ SYBR® Lo-ROX kit of the company Bioline in a reaction volume of about 10 μl.

Figure 3:
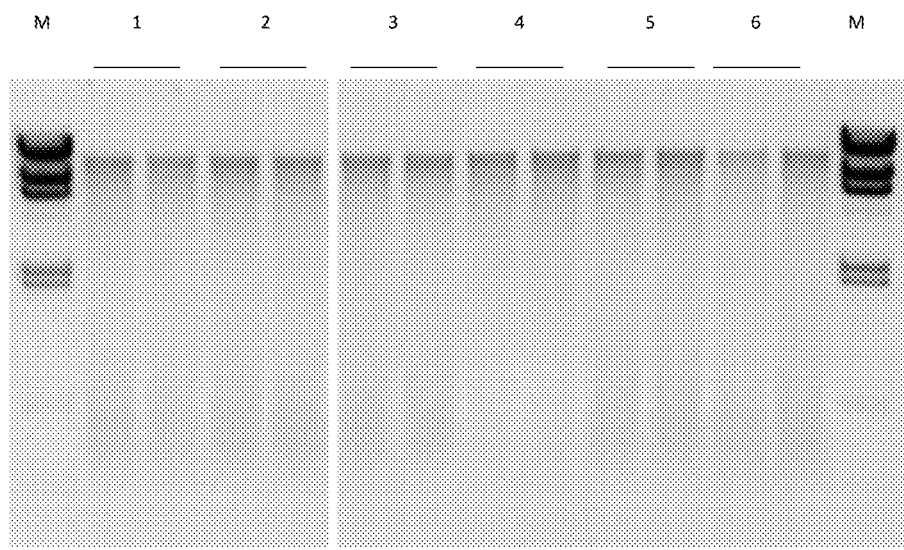

Here, it can be seen that the use of a washing solution containing an amine compound has an advantage over washing solutions containing chaotropic salts, since, despite a comparable DNA quantity (see FIG. 3), an amplification by means of qPCR could not be achieved.

Example 4

For each extraction, about 250 mg of a soil sample was lysed as described in the Test performance. Subsequently, about 400 μl of the respective binder solution (see Table 1) and about 25 μl of NucleoMag® B beads (carboxylated particles containing superparamagnetic particles in a range of sizes of from about 0.5 to about 10 μm) per sample were added. Subsequently, the magnetic particles were incubated with the washing solutions listed in Table 1 as described in the Test performance. After a drying step, the DNA was released from the magnetic particles by adding about 100 μl elution buffer (about 5 mM Tris/HCl, about pH 8.5), and separated off.

TABLE 4

Survey of the combinations of binder and washing solutions employed

| | Binder solution | Washing solution 1 | Washing solution 2 | Washing solution 3 | Washing solution 4 |
|---|---|---|---|---|---|
| Variant 1 | A (400 μl) | W1 (600 μl) | W2 (600 μl) | 80% EtOH (v/v) (600 μl) | 80% EtOH (v/v) (600 μl) |
| Variant 2 | A (400 μl) | W4 (600 μl) | W2 (600 μl) | 80% EtOH (v/v) (600 μl) | 80% EtOH (v/v) (600 μl) |
| Variant 3 | A (400 μl) | W4 (600 μl) | W4 (600 μl) | W3 (600 μl) | 80% EtOH (v/v) (600 μl) |
| Variant 4 | B (400 μl) | W1 (600 μl) | W2 (600 μl) | 80% EtOH (v/v) (600 μl) | 80% EtOH (v/v) (600 μl) |
| Variant 5 | B (400 μl) | W4 (600 μl) | W4 (600 μl) | 80% EtOH (v/v) (600 μl) | 80% EtOH (v/v) (600 μl) |
| Variant 6 | B (400 μl) | W5 (600 μl) | W5 (600 μl) | W3 (600 μl) | 80% EtOH (v/v) (600 μl) |

Analysis of the Eluates—Photometric Measurement

The photometric measurement at 300 nm can be used as an indicator of a brown color. The higher the absorption at 300 nm, the more discolored the eluates usually are, which indicates an entrainment of humic substances. Therefore, values that are as low as possible, for example, below about 0.075, are preferred.

The results are represented below in Table 5. They show that the use of a washing solution containing an amine compound or of the above described binder solution already leads to an absorption at 300 nm that is lower by a factor of five to six. The combination of the washing solution containing the amine compound and the binder solution results in an absorption that is lower by a factor of ten, which is comparable to that of the reference. Thus, the data show that the combination proves to be particularly advantageous.

TABLE 5

Absorption of the eluate fractions at 300 nm

| | Variant 1 | Variant 2 | Variant 3 | Variant 4 | Variant 5 | Variant 6 | Reference |
|---|---|---|---|---|---|---|---|
| Eluate 1 | 0.73 | 0.32 | 0.10 | 0.12 | 0.11 | 0.06 | 0.07 |
| Eluate 2 | 0.51 | 0.29 | 0.11 | 0.12 | 0.11 | 0.06 | 0.05 |

Electrophoretic and Photometric Analysis of the DNA Yield

Figure 4:
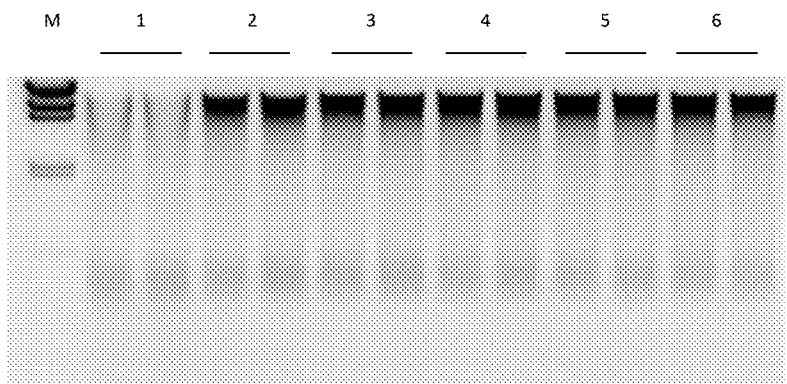

All in all, about 15 μl each of the eluates was separated by TAE gel electrophoresis (see FIG. 4). From the gel image, it can be determined that a comparable amount of DNA, visible as a distinct high-molecular weight band, could be isolated using the variants 2-6, while the DNA merely appears as a high-molecular weight cloud in eluates of variant 1.

Although a comparable amount of DNA can be seen according to the gel image, the photometrically determined yields (Table 6) are highly differing, which is also another indication of the entrainment of humic substances in variants 1-5. Only the combination of said binder solution and washing solution within one method results in a significant depletion of humic substances.

TABLE 6

Photometrically determined yield in μg

| | Variant 1 | Variant 2 | Variant 3 | Variant 4 | Variant 5 | Variant 6 |
|---|---|---|---|---|---|---|
| Eluate 1 | 9.7 | 5.6 | 3.2 | 3.2 | 3.3 | 2.2 |
| Eluate 2 | 9.9 | 5.5 | 3.2 | 3.2 | 3.0 | 2.3 |

Analysis of Enzyme Inhibition by qPCR

Further, the entrainment of humic substances was analyzed from the enzymatic inhibition within a qPCR. Those skilled in the art are aware that humic substances can inhibit enzymes such as thermostable DNA polymerases.

In the present Example, a fragment of a 16s rRNA gene was amplified with the forward primer AGAGTTTGATCCTGGCTCAG (SEQ ID NO: 3) and reverse primer AAGGAGGTGATCCAGCCGCA (SEQ ID NO: 4) by quantitative PCR using the Maxima SYBR Green qPCR Master Mix kit of the company Thermo Scientific™ in a reaction volume of about 12.5 μl.

The results of the qPCR are represented in Table 7 as Ct values, wherein an amplification can be detected for variants 2-6. The results of variant 1 indicate a complete inhibition of the enzymatic reaction. While no significant difference in concentration can be seen within the gel image in variants 2-6, the qPCR results are highly differing from one another. This difference can be explained by a reduction of enzymatic activity within the PCR as such, because a doubling of the DNA did not take place here. The relative DNA amounts quantified by qPCR are represented in Table 8. Here too, it is seen that only the combination of the binding and washing solutions results in a significant improvement in terms of amplification.

TABLE 7

Ct values of the eluates - qPCR

|  | Variant 1 | Var. 2 | Var. 3 | Var. 4 | Var. 5 | Var. 6 |
| --- | --- | --- | --- | --- | --- | --- |
| Eluate 1 | no amplification | 27.91 | 15.78 | 15.46 | 14.84 | 14.27 |
| Eluate 2 | no amplification | 27.54 | 15.86 | 15.61 | 14.85 | 14.44 |

TABLE 8

Relative Quantified DNA amount as compared to the reference

|  | Variant 1 | Var. 2 | Var. 3 | Var. 4 | Var. 5 | Var. 6 |
| --- | --- | --- | --- | --- | --- | --- |
| Eluate 1 | — | 0.01% | 36.06% | 44.09% | 71.14% | 100% |

---

The invention claimed is:

1. A method for isolating nucleic acids from a biological sample or an environmental sample and depleting contaminants/humic substances from the biological sample, comprising
    (a) lysing said biological sample;
    (b) adding a binder solution that is free from chaotropic salts, comprising at least one organic solvent selected from the group consisting of cyclic $C_{2-4}$-alkylene carbonates, $C_{2-3}$-alkylene glycol diacetates, and derivatives thereof, and at least one non-ionic surfactant, and a nucleic acid-binding solid phase to the lysed sample, and separating the solid phase with the nucleic acids bound thereto;
    (c) washing the separated solid phase with the nucleic acids bound thereto once or several times with the same or different washing solutions (A) and (B) that contain at least one amine compound (A) or are free of amine compounds (B), wherein at least one washing step with a washing solution (A) is performed; and
    (d) desorbing the nucleic acids from the washed solid phase by adding an aqueous elution buffer.

2. The method according to claim 1, wherein not only the binder solution of step (b) but also one or more of the solutions selected from the group consisting of the washing solution(s) (A) or (B) of step (c), and the elution buffer of step (d) are free of chaotropic salts.

3. The method according to claim 1, wherein said lysis is effected by mechanical and/or enzymatic lysis and by using a lysing solution.

4. The method according to claim 3, wherein said lysing solution contains a concentration of ≤2% (w/v) EDTA, from about 0.4% to about 2.5% (w/v) SDS, and/or ≤2% (w/v) of another anionic surfactant.

5. The method according to claim 3, wherein not only the binder solution of step (b) but also one or more of the solutions selected from the group consisting of the lysing solution of step (a), the washing solution(s) (A) or (B) of step (c), and the elution buffer of step (d) are free of chaotropic salts.

6. The method according to claim 5, wherein neither the lysing solution of step (a), nor the binder solution of step (b), nor the elution buffer of step (d) contains chaotropic salts, and only one of the washing solutions (A) or (B) of step (c) contains chaotropic salts.

7. The method according to claim 1, wherein, in the binder solution, said cyclic $C_{2-4}$-alkylene carbonate is selected from the group consisting of butylene carbonate, propylene carbonate, ethylene carbonate, and derivatives thereof, and said $C_{2-3}$-alkylene glycol diacetate is selected from the group consisting of ethylene glycol diacetate, propylene glycol diacetate, and derivatives thereof.

8. The method according to claim 7, wherein the binder solution contains at least one compound selected from the group consisting of butylene carbonate, propylene carbonate, ethylene carbonate, and ethylene glycol diacetate.

9. The method according to claim 1, wherein, in the binder solution, said at least one non-ionic surfactant is selected from the group consisting of polyoxyethylene derivatives of sorbitan monolaureate, sorbitan monopalmitate, and sorbitan monooleate, and polyoxyethylene derivatives of fatty alcohols.

10. The method according to claim 9, wherein, in the binder solution comprises polyoxyethylene(20) sorbitan monolaureate.

11. The method according to claim 1, wherein, in the binder solution, the ratio (v/v) of organic solvent to non-ionic surfactant is from about 80:20 to about 50:50, or is from about 75:25 to about 55:45, or is about 70:30.

12. The method according to claim 1, wherein, in step (b), the nucleic acid-binding solid phase is magnetic particles.

13. The method according to claim 1, wherein, in step (b), the amount of added binder solution, as a ratio to the volume of lysed sample, is from about 10:1 to about 1:10 (v/v), or is from about 3:1 to about 1:3 (v/v), or is from about 2:1 to about 1:1 (v/v).

14. The method according to claim 1, wherein, in step (b), the amount of added solid phase, as a ratio to the volume of lysed sample, is from about 1:10 to about 1:50 (v/v), or is from about 1:20 to about 1:40 (v/v), or is about 1:25 (v/v).

15. The method according to claim 1, wherein said washing solutions containing at least one amine compound (A) in step (c) contains at least one organic amine compound having at least two carbon atoms and a molecular weight of ≤500 g/mol, and at least one solvent other than the amine compound.

16. The method according to claim 1, wherein said washing solutions containing at least one amine compound (A) in step (c) has a pH at 20° C. within a range of from pH 3.0 to pH 8.5.

17. The method according to claim 1, wherein the volume of said washing solutions containing at least one amine compound (A) in step (c) is 10 times to 50 times that of the nucleic acid-binding solid phase employed in step (b).

18. The method according to claim 1, wherein, in said washing solutions containing at least one amine compound (A) in step (c), said at least one organic amine compound is selected from the group consisting of compounds of the general formula (I)

$$N(R^1)(R^2)(R^3) \qquad (I),$$

wherein $R^1$, $R^2$ and $R^3$ are independently a hydrogen atom, a ($C_{1-6}$)-alkyl group, a ($C_{1-6}$)-monohydroxyalkyl group, a ($C_{2-6}$)-dihydroxyalkyl group, or a ($C_{3-6}$)-trihydroxyalkyl group, with the proviso that at least one of radicals $R^1$, $R^2$ and $R^3$ is not a hydrogen atom.

19. The method according to claim 1, wherein said amine compound is triethylamine, triethanolamine, 2-amino-2-(hydroxymethyl)propane-1,3-diol (TRIS), 2,2-bis(hydroxymethyl)-2,2',2''-nitrilotriethanol (BIS-TRIS), 1,3-bis[tris(hydroxymethyl)methylamino]propane (BIS-TRIS propane), or a combination thereof.

20. The method according to claim 1, wherein said amine compound is bis-tris and/or triethanolamine.

21. The method according to claim 1, wherein, in said washing solutions containing at least one amine compound (A) in step (c), said solvent other than the amine compound is selected from the group consisting of salt-containing water-alcohol mixtures, salt-containing aqueous solutions, salt-containing alcoholic solutions, and a salt-containing alcohol-water mixtures.

22. The method according to claim 1, wherein said solvent other than the amine compound is an ethanol-water mixture, which may be free of chaotropic salts or may contain chaotropic salts.

23. The method according to claim 1, wherein, in said washing solutions containing at least one amine compound (A) in step (c), the washing solution(s) (A) of step (c) contains the organic amine compound in a concentration of from about 200 mmol/l to about 1000 mmol/l, or in a concentration of from about 200 mmol/l to about 800 mmol/l.

24. The method according to claim 1, wherein, in step (c), said washing with said washing solution(s) comprising an amine compound (A) is followed by one or several washings with washing solution(s) free of amino compounds (B).

25. The method according to claim 1, wherein said washing solution(s) (B) are selected from the group consisting of salt-containing alcoholic solutions, salt-containing aqueous solutions, and salt-containing alcohol-water mixtures.

26. The method according to claim 25, wherein the washing solutions (B) are selected from the group consisting of aqueous solutions that are free of chaotropic salts, aqueous solutions that contain chaotropic salts, ethanol-water mixtures that are free of chaotropic salts, ethanol-water mixtures that contain chaotropic salts, ethanolic solutions that are free of chaotropic salts and ethanolic solutions that contain chaotropic salts.

27. The method according to claim 1, wherein the volume of the washing solution (A) is 10 times to 50 times that of the nucleic acid-binding solid phase employed in step (b).

28. The method according to claim 1, wherein only one of washing solutions (A) and (B) contains chaotropic salts.

29. The method according to claim 1, wherein the elution buffer of step (d) is an alkaline low-salt buffer.

30. The method according to claim 1, wherein the volume of the elution buffer is about 1 to about 20 times the volume of the solid phase employed in step (b).

31. A kit for isolating nucleic acids from a biological sample, comprising
(I) a binder solution that is free from chaotropic salts and that comprises at least one organic solvent selected from cyclic $C_{2-4}$-alkylene carbonates, $C_{2-3}$-alkylene glycol diacetates, and derivatives thereof, and at least one non-ionic surfactant, and
(II) one or more washing solutions containing one or more amine compounds.

32. The kit of claim 31, wherein, in the binder solution, said cyclic $C_{2-4}$-alkylene carbonate is butylene carbonate, propylene carbonate, ethylene carbonate, or a derivative thereof, and said $C_{2-3}$-alkylene glycol diacetate is ethylene glycol diacetate, propylene glycol diacetate, or a derivative thereof; or wherein the binder solution contains at least one of butylene carbonate, propylene carbonate, ethylene carbonate, and ethylene glycol diacetate; or wherein, in the binder solution, said at least one non-ionic surfactant is a polyoxyethylene derivative of sorbitan monolaureate, sorbitan monopalmitate, or sorbitan monooleate, or a polyoxyethylene derivative of a fatty alcohol; or wherein, the binder solution comprises polyoxyethylene(20) sorbitan monolaureate; or wherein, in the binder solution, the ratio (v/v) of organic solvent to non-ionic surfactant is from about 80:20 to about 50:50, or is from about 75:25 to about 55:45, or is about 70:30; or wherein the nucleic acid-binding solid phase is magnetic particles; or wherein the amount of added binder solution, as a ratio to the volume of lysed sample, is from about 10:1 to about 1:10 (v/v), or is from about 3:1 to about 1:3 (v/v), or is from about 2:1 to about 1:1 (v/v); or wherein the amount of added solid phase, as a ratio to the volume of lysed sample, is from about 1:10 to about 1:50 (v/v), or is from about 1:20 to about 1:40 (v/v), or is about 1:25 (v/v); and wherein said washing solutions containing at least one amine compound (A) in step (c) contains at least one organic amine compound having at least two carbon atoms and a molecular weight of ≤500 g/mol, and at least one solvent other than the amine compound; or wherein said washing solutions containing at least one amine compound (A) has a pH at 20° C. within a range of from pH 3.0 to pH 8.5; or wherein the volume of said washing solutions containing at least one amine compound (A) is 10 times to 50 times that of the nucleic acid-binding solid phase employed; or wherein, in said washing solutions containing at least one amine compound (A), said at least one organic amine compound is selected from the group consisting of compounds of the general formula (I)

$$N(R^1)(R^2)(R^3) \hspace{2cm} (I),$$

wherein $R^1$, $R^2$ and $R^3$ are independently a hydrogen atom, a $(C_{1-6})$-alkyl group, a $(C_{1-6})$-monohydroxyalkyl group, a $(C_{2-6})$-dihydroxyalkyl group, or a $(C_{3-6})$-trihydroxyalkyl group, with the proviso that at least one of radicals $R^1$, $R^2$ and $R^3$ is not a hydrogen atom; or wherein said amine compound is triethylamine, triethanolamine, 2-amino-2-(hydroxymethyl)propane-1,3-diol (TRIS), 2,2-bis(hydroxymethyl)-2,2',2''-nitrilotriethanol (BIS-TRIS), 1,3-bis[tris(hydroxy-methyl)methylamino]propane (BIS-TRIS propane), or a combination thereof; or wherein, in said washing solutions containing at least one amine compound (A), said solvent other than the amine compound is a salt-containing water-alcohol mixture, a salt-containing aqueous solution, a salt-containing alcoholic solution, and/or a salt-containing alcohol-water mixture; or wherein, said washing solutions containing at least one amine compound (A) contain the organic amine compound in a concentration of from about 200 mmol/l to about 1000 mmol/l, or in a concentration of from about 200 mmol/l to about 800 mmol/l.

33. The kit of claim 31 further comprising a solid phase that binds nucleic acids.

34. The kit according to claim 31, further comprising one or more of the solutions/buffers selected from
(III) lysing solutions that may be free of chaotropic salts,
(IV) one or more washing solutions that are free of amine compounds selected from the group consisting of aqueous solutions that are free of chaotropic salts, aqueous solutions that contain chaotropic salts, ethanol-water mixtures that are free of chaotropic salts, ethanol-water mixtures that contain chaotropic salts, ethanolic solutions that are free of chaotropic salts and ethanolic solutions that contain chaotropic salts, and
(V) aqueous elution buffers selected from the group consisting of elution buffers free of chaotropic salts and alkaline low-salt buffers.

35. The kit according to claim 31, which is for isolating nucleic acids from a biological sample or an environmental sample and depleting contaminants/humic substances from a biological sample.

* * * * *